United States Patent

Krämer

[11] Patent Number: 5,866,015
[45] Date of Patent: Feb. 2, 1999

[54] METHOD FOR DETERMINING HEMODYNAMIC PARAMETERS DURING AN EXTRACORPOREAL HEMOTHERAPY AND RELATED DEVICE

[75] Inventor: Matthias Krämer, Obenursel, Germany

[73] Assignee: Fresenius AG, Bad Homburg, Germany

[21] Appl. No.: 743,778

[22] Filed: Nov. 7, 1996

[30] Foreign Application Priority Data

Nov. 9, 1995 [DE] Germany ............... 195 41 783.6

[51] Int. Cl.$^6$ .................. B01D 61/32; B01D 61/30
[52] U.S. Cl. .................. 210/739; 210/87; 210/143; 210/149; 210/646; 210/742; 210/929; 604/4; 604/31; 364/510
[58] Field of Search ................. 210/85, 87, 96.1, 210/143, 321.65, 645, 646, 929, 329, 739, 742, 149, 416.1; 604/4, 5, 6, 27–31; 364/510

[56] References Cited

U.S. PATENT DOCUMENTS

| | | | |
|---|---|---|---|
| 5,092,836 | 3/1992 | Polaschegg | 210/646 |
| 5,312,550 | 5/1994 | Hester | 210/646 |
| 5,453,576 | 9/1995 | Krivitski . | |
| 5,510,716 | 4/1996 | Buffaloe et al. | 210/646 |
| 5,588,959 | 12/1996 | Ahmad et al. | 604/6 |
| 5,685,989 | 11/1997 | Krivitski et al. | 210/742 |

FOREIGN PATENT DOCUMENTS

| | | |
|---|---|---|
| 0 590 810 | 4/1994 | European Pat. Off. . |
| 38 17 603 | 11/1989 | Germany . |

*Primary Examiner*—Joseph W. Drodge
*Attorney, Agent, or Firm*—Kenyon & Kenyon

[57] ABSTRACT

A method and a device for determining hemodynamic parameters during an extracorporeal hemotherapy, in which the blood arrives via the arterial branch (20) of the extracorporeal circuit (9) of the hemotherapeutic device (7), which is in fluid communication with arterial section (21) of a fistula (6), into dialyzer (10) or into a filter of the hemotherapeutic device and is recirculated via the venous branch (22) of the extracorporeal circuit (9), which is in fluid communication with venous section (23) of fistula (6). The temperature $T_A$ prevailing in the arterial branch (20) of the extracorporeal circuit (9) is measured under a changing blood flow, the temperature $T_V$ of the venous branch (22) of the extracorporeal circuit being kept constant. From the determined value pairs of the arterial temperature $T_A$ and of the extracorporeal blood flow $Q_B$, those parameters of a predetermined function $T_A(Q_B)$ representing the temperature in the arterial branch of the extracorporeal circuit (9) are defined as a function of the blood flow $Q_B$, which are drawn upon to determine the fistula flow $Q_F$ and/or the body temperature $T_B$ and/or the cardiac output (l/min) CO.

18 Claims, 2 Drawing Sheets

5,866,015

METHOD FOR DETERMINING HEMODYNAMIC PARAMETERS DURING AN EXTRACORPOREAL HEMOTHERAPY AND RELATED DEVICE

BACKGROUND OF THE INVENTION

1. Field of the Invention

The invention is directed to a method for operating a hemotherapeutic device for determining hemodynamic parameters during an extracorporeal hemotherapy, as well as to a device for determining hemodynamic parameters during an extracorporeal hemotherapy.

2. Description of Related Art

In methods used in chronic blood purification therapy, such as hemodialysis, hemofiltration, and hemodiafiltration, blood is circulated through an extracorporeal circuit. Often an arteriovenous fistula is surgically inserted as an access route to the vascular system. It is likewise possible for an implant to be used. The term "fistula" referred to in the following is understood to be any type of connection between a vein and an artery of a patient.

The purpose of the vascular access route is to supply a blood flow at least as great as the extracorporeal blood flow specified by the pump in the extracorporeal hemodialysis circuit. Should such a blood flow not be supplied, due, for example, to vessel constrictions (stenoses), the arterial needle may possibly attach itself by suction to the vascular wall, thereby interrupting the extracorporeal circuit. In most cases, however, a portion of the extradorporeal blood flow, namely the difference between the extracorporeal blood flow and the blood flow streaming into the fistula, is recirculated in the extracorporeal circuit. This phenomenon is described as recirculation.

A consequence of the fistula recirculation is a reduction in the quantity of substances requiring dialysis that is removed from the body per unit of time. The recirculating portion does not pass through the body's capillary system and, therefore, is not invaded again by toxic substances. Therefore, this portion has a lesser role in the blood purification. If the effectiveness of the dialysis is substantially reduced because of failure to detect and compensate for the recirculation, then the morbidity rate of such patients will rise over the long term. Thus, an important method for assuring quality in a dialysis treatment is to measure the quality of the vascular access route.

Various methods are known for measuring fistula recirculation. Common to all of them is the measurement of a physical-chemical blood property, which must be variable in the venous blood. The physical-chemical property can be altered through direct action of the user or indirectly via the dialysate preparation unit. The occurrence of fistula recirculation can subsequently be determined or quantified, in that a change in this property is also verified in the arterial blood.

Such a method is described by U.S. Pat. No. 5,312,550 and EP 0 590 810 A1, where an indicator solution is injected into the venous line and monitored for its concentration in the arterial blood. It is also possible to bypass the step of injecting an indicator solution, because when fistula recirculation is at hand, a short-term temperature drop is produced in the dialyzing fluid circuit, and then spreads to the venous branch of the extracorporeal circuit, to then lead to a detectable rise in temperature in the arterial branch of the extracorporeal circuit (M. Kramer and H. D. Polaschegg, EDTNA-ERCA J. 19, 6 (1993)).

The measured recirculation cannot always be readily interpreted, since this technical parameter is not easily correlated with the actual physiological parameter of interest, namely the blood flow to fistula $Q_F$. Thus, for example, in spite of constant fistula flow $Q_F$, the recirculation varies with the blood flow $Q_B$. Moreover, many measuring processes not only record the fistula recirculation, but also the sum of the fistula and cardiopulmonary recirculation (M. Kramer and H. D. Polaschegg, EDTNA-ERCA J. 19, 6 (1993)). The cardiopulmonary recirculation, which is defined as the fistula flow's fractional share in the cardiac output (l/min), refers to already dialyzed blood, which arrives via the cardiopulmonary system directly in the arterial branch of the extracorporeal circuit without passing through the capillary system. The change in blood temperature that occurs in the arterial blood pathway before the onset of the fistula recirculation is attributable to the cardiopulmonary recirculation. In addition, because the fistula recirculation and the cardiopulmonary recirculation overlap, it is more difficult to interpret the measuring results.

Therefore, it would be beneficial to directly measure fistula flow $Q_F$. *The Journal of Medical Engineering and Technology* 8, 118 (1984), a publication of Aldridge et al., describes the first attempts made to perform such measurements. Individual recirculation measurements are taken using the thermodilution method following the injection of a bolus of a cold saline solution. The measurements are repeated with blood flow being incrementally increased until a noticeable recirculation is ascertained. At this blood flow rate, the fistula flow $Q_F$ is then exceeded. Associated with this method is the problem that the fistula flow is limited only to the measuring interval and, therefore, cannot be precisely determined, and that the measurement is costly because of the continuous bolus injection. It is more significant, however, that this work does not consider that a recirculation, namely the cardiopulmonary recirculation, is present in vivo in every blood flow, and overlaps the fistula recirculation. Aldridge et al. discuss still a second method which seems better suited for detecting fistula flow. When a variation in the extracorporeal blood flow $Q_B$ causes it to closely approach fistula flow $Q_F$, an oscillation is observed in the arterial temperature TA. This results from the periodically fluctuating pressure conditions in the fistula caused by the action of the blood pump, usually designed as a roller pump. The disadvantage of this method is that the "correct" blood flow $Q_B=Q_F$ can only be found tediously by varying $Q_B$, and by checking TA for the presence of oscillations. Moreover, the temperature sensory mechanism in the arterial system must exhibit a very low response time, since the oscillation period lies within the range of a few tenths of a second up to about one second. This requirement can only be met, intra-arterially, by placing the sensors directly in the bloodstream, which is not a viable method for routine treatments.

SUMMARY OF THE INVENTION

An object of the invention is to specify a method for operating a hemotherapeutic device, which will enable hemodynamic parameters to be determined with substantial accuracy during an extracorporeal blood hemotherapy. A further object of the invention is to provide a device which will enable hemodynamic parameters to be determined with substantial reliability. These and other objects of the invention which will become apparent from the following detailed description are achieved as follows.

The invention is a method for operating a hemotherapeutic device for determining hemodynamic parameters during an extracorporeal hemotherapy. The blood arrives via an arterial branch of an extracorporeal circuit, which is in fluid communication with an arterial section of a fistula, into dialyzer or into the filter of a hemotherapeutic device, and is recirculated via a venous branch of the extracorporeal circuit, which is in fluid communication with a venous section of the fistula. A blood pump is connected into the extracorporeal circuit.

The invention includes the following steps:

measuring a physical or chemical characteristic quantity $X_A$ of the blood in arterial branch of the extracorporeal circuit, the physical or chemical characteristic quantity being a blood property which has a different value in the venous branch of the extracorporeal circuit than it does in the blood flowing to fistula;

varying the delivery rate of the blood pump in the extracorporeal circuit;

storing the values of the extracorporeal blood flow $Q_B$ stipulated by the delivery rate of the blood pump and the measured values of the physical or chemical characteristic quantity of the blood in the arterial branch of the extracorporeal circuit; and determining a value of the blood flow from the stored sequence of value pairs of the physical or chemical characteristic quantity $X_A$ of the blood in the arterial branch of the extracorporeal circuit and of extracorporeal blood flow $Q_B$, at which value, after it is exceeded, the amount of the change in the physical or chemical characteristic quantity $X_A$ within a specific blood flow interval is greater than a predetermined limiting value. The fistula flow is inferred from the determined blood flow value.

The invention is also a device for determining hemodynamic parameters during an extracorporeal hemotherapy. The device includes:

an arterial measuring device for measuring a physical or chemical characteristic quantity $X_A$ of the blood in the arterial branch of extracorporeal circuit, the physical or chemical characteristic quantity being a blood property which has a different value in venous branch of extracorporeal circuit than it does in the blood flowing into fistula;

a control unit for altering the delivery rate of blood pump;

a memory unit which is so conceived that the values of blood flow $Q_B$ predetermined by the delivery rate of blood pump and the values of the physical or chemical characteristic quantity $X_A$ measured using arterial measuring device are able to be stored in arterial branch of extracorporeal circuit; and a processor which is able to determine a value of the blood flow from the stored sequence of value pairs of the physical or chemical characteristic quantity $X_A$ of the blood in arterial branch of extracorporeal circuit and of extracorporeal blood flow $Q_B$, at which value, after it is exceeded, the amount of the change in the physical or chemical characteristic quantity within a specific blood flow interval is greater than a predetermined limiting value, fistula flow $Q_F$ being inferable from the determined blood flow value.

DETAILED DESCRIPTION OF THE INVENTION

Figure 1:
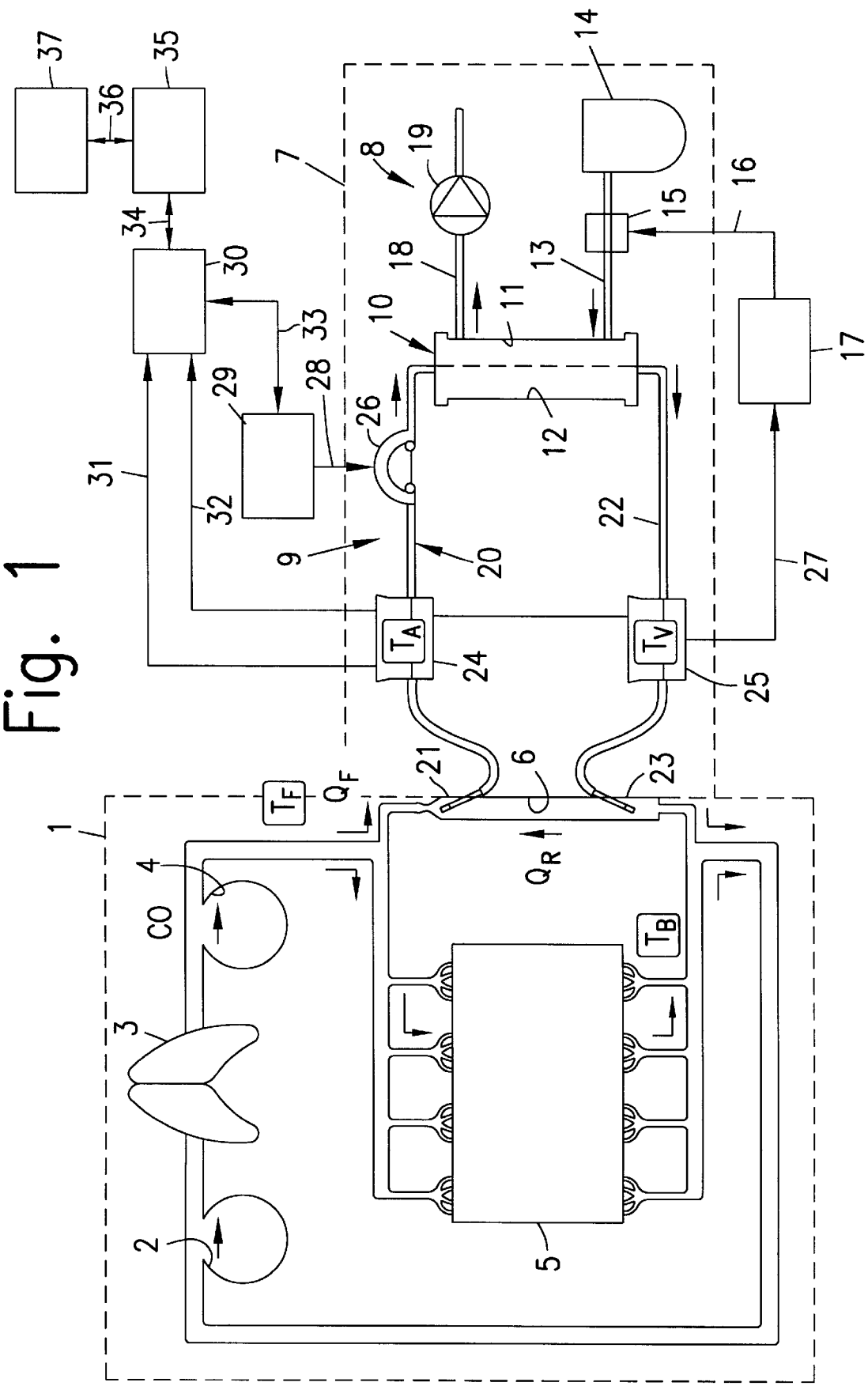
FIG. 1 illustrates a device according to the invention for determining hemodynamic parameters, together with a dialyzer, in a schematic representation, inclusive of the intracorporeal circulatory system.

In the method according to the invention for determining hemodynamic parameters, such as fistula flow, cardiac output (l/min) and, in the case of temperature measurement, body temperature, a physical or a chemical characteristic [quantity] of the blood is measured in the arterial branch of the extracorporeal circuit. Any physical or chemical quantity that fulfills the following conditions can be measured. It must have a different value in the venous blood (i.e., in the blood flowing back from the extracorporeal circuit into the venous part of the patient's fistula) than it does in the blood flowing to the fistula. The value of the physical or chemical characteristic [quantity] in a mixture of two partial blood volumes ($V_1$ and $V_2$) must be produced, analogously to the temperature T, with sufficient accuracy, in accordance with the following mixture equation:

$$V_1 \cdot T_1 + V_2 \cdot T_2 = (V_1 + V_2) \cdot T_M,$$

$V_1$ and $V_2$ being the partial volumes and $T_1$ and $T_2$ being the values of the physical or chemical characteristic [quantity] to be measured in the two partial volumes, and $T_M$ being the value after the mixing operation.

In addition to measuring temperature as a physical or chemical characteristic [quantity], the concentration of a blood constituent, of the hematocrit [packed cell volume], can also be measured, as can the density, speed of sonic propagation, optical density, and conductivity or viscosity. These quantities can be determined using known measuring sensors.

It is beneficial for the blood temperature to be measured as a physical or chemical characteristic [quantity]. When measuring the blood temperature using the method according to the invention, besides fistula flow and cardiac output (l/min), it is also possible to determine body temperature, which is understood as the average temperature of the blood after it has passed through all capillary systems. There is no need then to inject an indicator solution.

It is assumed under the method of the invention that the physical or chemical characteristic [quantity], preferably the blood temperature, is kept constant in the venous branch of the extracorporeal circuit while the measured values are recorded. It is also assumed under the method of the invention that the physical or chemical characteristic [quantity] in the venous branch is known by its magnitude. If the physical or chemical characteristic [quantity] is neither constant nor known by its magnitude, then it must be measured and kept constant while the measured values are recorded.

The method according to the invention is based on the fact that the measuring curve existing in discrete measured values is able to be represented by two subfunctions, the first subfunction indicating the physical or chemical characteristic [quantity] as a function of the extracorporeal blood flow for blood flow values smaller than the fistula flow or equal to the fistula flow, and the second subfunction indicating the physical or chemical characteristic [quantity] as a function of the blood flow for blood flow values greater than or equal to the fistula flow. The intersection of the two subfunctions indicates the point where the extracorporeal blood flow equals fistula flow. Thus, from the "break point" of the characteristic function curve, i.e., from the discontinuity in the rise of the curve, the point is able to be defined where fistula recirculation begins, i.e., where blood flow equals fistula flow.

To determine the fistula flow, that value of the blood flow is determined from the stored sequence of value pairs of the physical or chemical characteristic [quantity] of the blood in the arterial branch of the extracorporeal circuit, at which value, after it is exceeded, the amount of the change in the physical or chemical characteristic [quantity] within a specific blood flow interval, i.e., the amount of the slope of the function representing the measured value pairs is greater than a predetermined limiting value. The slopes within the individual measuring intervals can be determined, for example, by calculating the difference quotients of the measured value pairs. The determined blood flow value represents an estimate of the fistula flow. When a very accurate determination of fistula flow is needed, the characteristic function curve for blood flow values existing in the sequence of value pairs is represented as a smaller curve than the estimate for the fistula flow by a first subfunction, while the characteristic function curve for blood flow values existing in the sequence of value pairs is shown as a larger curve than the estimate by a second subfunction.

The exact value of the fistula flow is then determined from the point of intersection of the two subfunctions. The subfunction for blood flow values smaller than or equal to fistula flow can be represented approximatively by a linear equation.

The average value of the physical or chemical characteristic [quantity] in the venous blood of the patient is obtained by extrapolating the characteristic function curve for blood flow values smaller than or equal to the fistula flow approaching a blood flow value of zero. In the case of a temperature measurement, the body temperature is able to be determined. After determining fistula flow and the average value of the physical-chemical property, the cardiac output (l/min) can be calculated.

The device according to the invention for determining hemodynamic parameters has an arterial measuring device for measuring the physical-chemical property in the arterial branch of the extracorporeal circuit, and a control unit for altering the delivery rate of the blood pump. Also provided are a memory unit for storing the values of the physical-chemical property and of the extracorporeal blood flow, and a processor [arithmetic unit] for determining the hemodynamic parameters from the stored value pairs. The device according to the invention can be integrated in known blood-purification devices, it being possible to employ components already existing in known hemotherapeutic devices.

If the physical or chemical characteristic [quantity] in the venous branch of the extracorporeal circuit is not constant, the device according to the invention advantageously has a regulating device to keep the physical or chemical characteristic [quantity] in the venous branch constant. In the case of a temperature measurement, for example, this can be realized as a temperature controller.

An exemplary embodiment of the device according to the invention for determining hemodynamic parameters and the operational method according to the invention for an extracorporeal hemotherapeutic device for determining hemodynamic parameters will now be explained with reference to FIGS. 1–3.

The device according to the invention for determining hemodynamic parameters can make up a separate assembly unit. However, it can also be a component of a dialyzer, especially as some of the components of the device according to the invention are already present in known dialyzers. The device according to the invention will be described in the following, together with the essential components of the dialyzer. In the exemplary embodiment, the temperature $T_A$ prevailing in the arterial branch of the extracorporeal circuit is measured as a physical or chemical characteristic quantity $X_A$, so that besides fistula flow $Q_F$, it is also possible to determine body temperature $T_B$, i.e., the average temperature of the blood after it passes through all capillary systems, and the cardiac output (l/min) CO.

Referring to FIG. 1, the intracorporeal circulatory system 1 includes the right ventricle 2 of the heart, lung 3, left ventricle 4, and all capillary systems of the body in the internal organs, muscular system, and skin 5. An arterio-venous fistula 6 is inserted to create an access route to the vascular system.

Dialyzer 7 essentially includes a dialyzing fluid section 8 and an extracorporeal blood circuit 9, between which is situated a dialyzer 10 having a dialyzing fluid compartment 11 and a blood compartment 12. Dialyzing fluid compartment 11 is connected upstream from dialyzer 10 via a dialyzing fluid line 13 to a dialyzing fluid source 14. Connected into dialyzing fluid line 13 is a temperature stabilizer 15, which communicates via a control line 16 with a regulating device 17. Connected to dialyzing fluid compartment 11 downstream of dialyzer 10 is another line 18, which has a dialyzing fluid pump 19.

Extracorporeal circuit 9 includes an arterial branch 20, which communicates with arterial section 21 of fistula 6, and comprises blood compartment 12 of dialyzer 10 and a venous branch 22, which communicates with the venous section 23 of fistula 6. Provided in arterial branch 20 and in venous branch 22 of the extracorporeal circuit is in each case a temperature-measuring device 24, 25 for measuring the arterial fistula temperature, i.e., the blood temperature following ingress into arterial branch 20 of extracorporeal circuit 9 or for measuring the venous fistula temperature, i.e., the blood temperature following ingress into venous branch 22 of the extracorporeal circuit.

Also arranged in arterial branch 20 of extracorporeal circuit 9 is a blood pump 26. The venous temperature-measuring device 25 is connected via a line 27 to regulating device 17. Temperature stabilizer 15 in dialyzing fluid section 8 of dialyzer 7 is driven by regulating device 17 to keep the temperature in venous branch 22 of extracorporeal circuit 9 constant. Other customary dialyzer components, such as drip chambers and stop clamps, are not shown in FIG. 1.

Blood pump 26 in arterial branch 20 of the extracorporeal circuit is connected via a control line 28 to a control unit 29, which is able to vary the delivery rate of the blood pump within certain ranges. Furthermore, a memory unit 30 is provided, which via a data line 31 receives the measured values of arterial temperature-measuring device 24 and stores them in chronological sequence. In addition, via a data line 32, memory unit 30 stores the constant temperature value of the venous temperature-measuring device 25. Memory unit 30 is linked via a line 33 to control unit 29. Via line 33, memory unit 30 receives the value of the extracorporeal blood flow corresponding to the adjusted delivery rate of blood pump 26 and stores said value. Memory unit 30 communicates via a data line 34 with a processor [arithmetic unit] 35, which is linked, in turn, via a data line 36 to a display unit 37 to indicate the determined hemodynamic parameters. The processor can be designed as a known digital computer.

The measuring principle will now be explained.

The blood emitted from left ventricle 4 flows for the most part into the capillary systems of all organs, and to a limited extent into the fistula. If the blood flow in the extracorporeal circuit is smaller than the blood flow streaming into or out of the fistula, then the fistula blood flows, on the one hand, through extracorporeal circuit 9 and, on the other hand, through fistula 6. However, when the extracorporeal blood flow is greater than the fistula flow, then blood recirculates out of extracorporeal circuit 9, fistula 6 being traversed by the flow from venous connection 23 to arterial connection 21. The extracorporeal blood, the blood flowing through fistula 6, and the blood coming from the capillary systems is finally reunited again when it returns to the heart.

The following designations refer to the temperatures and flows:

| | |
|---|---|
| $Q_F$ | the fistula flow, i.e., the flow into fistula 6 and, respectively, out of the fistula; |
| $Q_B$ | the blood flow in the extracorporeal circuit 9, |
| $Q_R$ | the recirculation flow, i.e., the flow between venous section 23 and arterial section 21 of fistula 6, when $Q_F \leq Q_B$; |
| CO | cardiac output (l/min); |
| $T_B$ | body temperature, i.e., the average temperature of the blood after passing through the capillary systems; |
| $T_F$ | fistula temperature, i.e., the temperature of the blood flowing into fistula 6; |
| $T_A$ | arterial fistula temperature, i.e., the blood temperature following ingress into arterial branch 20 of extracorporeal circuit; |
| $T_V$ | venous fistula temperature, i.e., the blood temperature following ingress into venous branch 22 of the extracorporeal circuit. |

The method according to the invention is based on the fact that the measured blood temperature $T_A$ in the arterial branch of the extracorporeal circuit is able to be represented as a function of the extracorporeal blood flow $Q_B$ by two subfunctions, the one subfunction indicating the arterial blood temperature $T_A$ for an extracorporeal blood flow smaller than or equal to the fistula flow, and the other subfunction indicating the arterial blood temperature $T_A$ given an extracorporeal blood flow greater than or equal to the fistula flow. The two subfunctions can be derived as explained in the following, the assumption being that the ultrafiltration is switched off during the measuring operation.

Let it be assumed that blood flow $Q_B$ in extracorporeal circuit 9 is smaller than or equal to fistula flow $Q_F$. The blood flowing into the right heart is composed of the three following components, namely of the blood flowing back from the capillary system to the heart, of the blood coming from extracorporeal circuit 9, and of the blood flowing through fistula 6, however not through the extracorporeal circuit. This yields the following mixture equation for the temperatures:

$$(CO-Q_F) \cdot T_B + Q_B \cdot T_V + (Q_F - Q_B) T_F = CO \cdot T_F$$

Since the arterial blood consists of only one component, namely the blood flowing to fistula 6, arterial fistula temperature $T_A$ equals fistula temperature $T_F$. This yields the following subfunction:

$$T_A(Q_B) = \frac{(CO - Q_F) \cdot T_B + Q_B \cdot T_V}{CO - Q_F + Q_B} \quad (1)$$

The above equation can also be expressed as follows:

$$T_A(Q_B) = (\gamma + \delta Q_B)/(\epsilon + Q_B)$$

where $\gamma = (CO - Q_F)T_B$, $\delta = T_V$, $\epsilon = CO - Q_F$ (1)

Let it be assumed that blood flow $Q_B$ in extracorporeal circuit 9 is greater than fistula flow $Q_F$. In this case, the blood flowing into arterial branch 20 of extracorporeal circuit 9 is composed of the blood flowing into fistula 6 and of the blood recirculating through the fistula, i.e., of the blood coming from venous branch 22 of extracorporeal circuit. This yields the following mixture equation for the temperatures:

$$Q_F \cdot T_F + Q_R T_V = Q_B T_A$$

The fistula blood is composed, as in the following, of the capillary blood and of the blood coming from extracorporeal circuit 9.

$$(CO - Q_F) \cdot T_B + Q_F T_V = CO \cdot T_F$$

With $Q_R = Q_B - Q_F$, from these two equations is derived the second subfunction:

$$T_A(Q_B) = \left(1 - \frac{Q_F}{CO}\right) \cdot \frac{Q_F}{Q_B} \cdot T_B + \frac{Q_F^2}{Q_B \cdot CO} \cdot T_V + \left(1 - \frac{Q_F}{Q_B}\right) \cdot T_V \quad (2)$$

The second subfunction can also be expressed as follows:

$$T_A(Q_B) = \alpha/Q_B + \beta$$

where $$\alpha = Q_F T_B (1 - Q_F/CO) + Q_F^2 T_V/CO - Q_F T_V, \quad \beta = T_V \quad (2)$$

Thus, the function $T_A(Q_B)$ is made up of the two subfunctions (1) and (2), in each case for the ranges $Q_F \geq Q_B$ and $Q_F < Q_B$.

Figure 2:
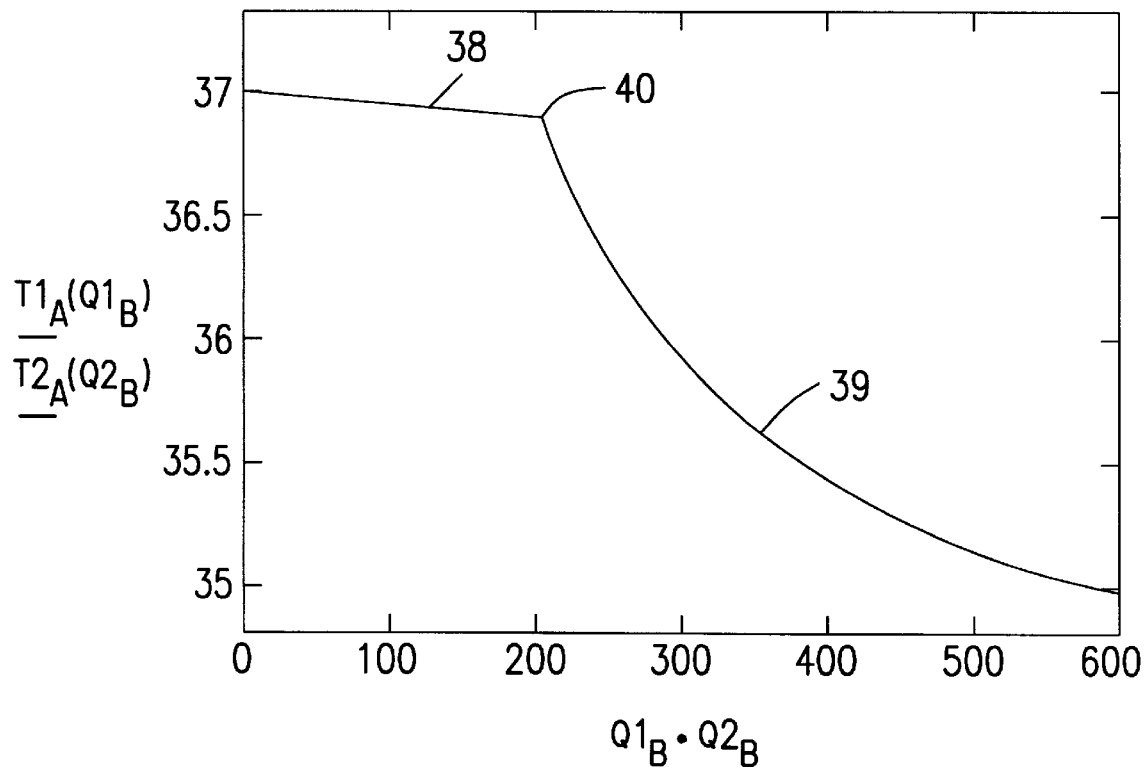
FIG. 2 is a graph of the temperature in the arterial branch of the extracorporeal circuit as a function of the extracorporeal blood flow.

FIG. 2 illustrates blood temperature $T_A$ in arterial branch 20 of extracorporeal circuit 9 as a function of extracorporeal blood flow $Q_B$ the active blood flow range in the hemodialysis of 100 to 600 ml/min being indicated on the horizontal axis. At the point where the slope of the curve exhibits a point of discontinuity, the extracorporeal blood flow is identical to the fistula flow. The characteristic function curve is calculated in accordance with equation (1) and (2), where CO=5 l/min, $Q_F$=200 ml/min, $T_B$=37° C. and $T_V$=34° C.

Figure 3:
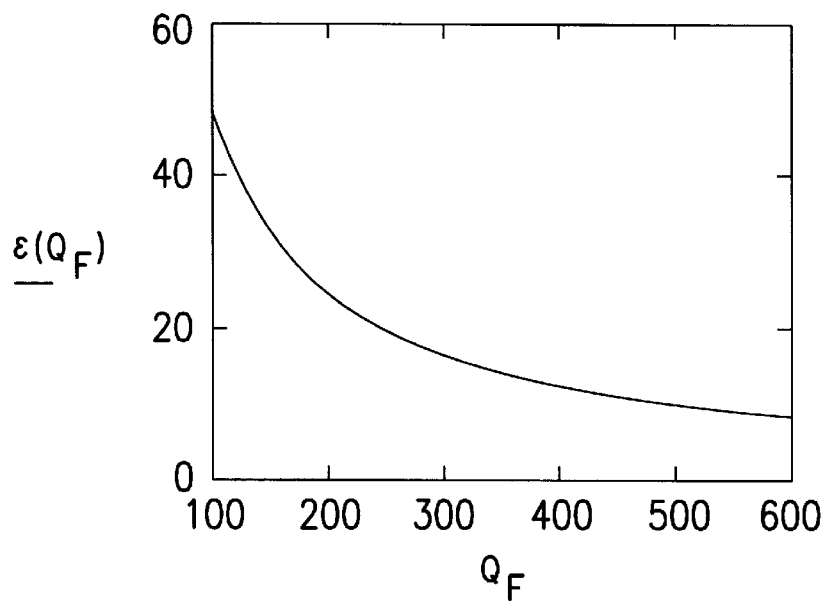
FIG. 3 graphically illustrates the relationship of the slopes of the two curve sections of the first and second subfunction for representing the measuring curve characteristic for an extracorporeal blood flow corresponding to the fistula flow.

FIG. 3 illustrates the relationship between the slopes of the two curve sections of function $T_A(Q_B)$ for the point of intersection where $Q_B = Q_F$. Values are produced as a function of fistula flow $Q_F$ between 50 ($Q_F$=100 ml/min) and 8.3 ($Q_F$=600 ml/min). Thus, the discontinuity in the curve slope can be detected definitively enough within the entire blood flow interval of 100 to 600 ml/min.

To determine the fistula flow, the delivery rate of blood pump 26, which predetermines the extracorporeal blood flow, is increased slowly starting from a predetermined lower limiting value of, for example, 100 ml/min up to an upper limiting value of, for example, 600 ml/min, the lower limiting value corresponding to an extracorporeal blood flow $Q_B$, which, in any case, is smaller than the fistula flow $Q_F$ to be expected, and the upper limiting value conforming to a corresponding blood flow, which, in any case, is greater than the fistula flow to be expected. The temperature $T_A$ of the blood in arterial branch 20 of extracorporeal circuit 9 is measured while the blood flow increases using arterial measuring device 24, and the values of the extracorporeal blood flow and of temperature $T_A$ are stored chronologically in memory unit 30.

The difference quotients are calculated in processor 35 from the stored sequence of value pairs. The calculated difference quotients of the value pairs are compared to a predetermined limiting value. In processor 35, that value of blood flow $Q_B$ in the extracorporeal circuit is now determined, at which value, after it is exceeded, the amounts of the determined difference quotients are greater than a specified limiting value, i.e., the point is determined where there is a substantial, sudden drop in the curve shown in FIG. 2. While the slope of the left curve section shown in FIG. 2 is, namely, small and nearly constant, in the case that blood flow $Q_B$ is greater than fistula flow $Q_F$, there is a sudden, sharp rise in the amount of the slope. The assumption is made in the measurement that the determined value of blood flow $Q_B$ corresponds to fistula flow $Q_F$. This value is stored as an estimate of the fistula flow in memory unit 30.

To be able to exactly determine the value of the fistula flow, i.e., as a value that is unaffected by possible fluctuations in the blood flow in the area of the fistula flow, in processor 35, the stored measured-value pairs for blood flow values $Q_B$ smaller than the estimated value for the fistula flow are adapted through the first subfunction (1), and the stored measured-value pairs for blood flow values greater than the estimate for the fistula flow are adapted through the second subfunction (2). It is advantageous in this case when measured-value pairs from a small range (e.g., ±30 ml/min) around containing the estimated value for the fistula flow are left out. The known numerical methods (e.g., Levenberg-Marquardt method) can be drawn upon to calculate the parameters of both equations. Sufficient accuracy is also generally achieved when in place of equation (1), a simple linear function is drawn upon to represent the curve shape. Processor 35 subsequently calculates the value of extracorporeal blood flow $Q_B$ which corresponds to fistula flow $Q_F$ by defining intersection point 40 of the two subfunctions 38 and 39. This value is stored in memory unit 30 and is indicated by display unit 37. To determine body temperature $T_B$, the left curve section represented by equation (1) in FIG. 2 is extrapolated in the processor approaching a blood flow value of 0 ($T_B$ $T_A(0)$). The temperature value for a blood flow value of 0, which cannot be ascertained by performing a measurement, corresponds to body temperature $T_B$. This is stored in memory unit 30 and indicated on display unit 37.

After fistula flow $Q_F$ and body temperature $T_B$ are determined and stored, the cardiac output (l/min) CO is calculated as follows in processor 35:

$$CO = Q_F \frac{T_V - T_B}{T_A(Q_F) - T_B} \quad (3)$$

Equation (3) follows from equation (1) with $Q_B = Q_F$.

This hemodynamic parameter is also shown on display unit 37.

Control unit 29 of the device according to the invention drives the individual system components in accordance with a predetermined program run, so that after manipulation of a push-button control (not shown in FIG. 1) to start the measurement, blood flow $Q_B$ is automatically altered within the interval of 100 to 600 ml/min, the measured values are recorded by temperature-measuring devices 24, 25 in the corresponding intervals and stored in memory unit 30 and, from the measured values, the hemodynamic parameters are calculated in processor 35 and indicated on display unit 37.

The method does not require any substantial changes in the extracorporeal circuit or in the safety concept of the dialysis device. There is no need to inject an indicator solution. Fistula flows can, in fact, only be measured within the adjustable blood flow range (approx. 100 to 600 ml/min), however, in practice this does not signify any restriction. If the fistula flow is greater than the adjustable blood flow, no problems will arise, namely, for the treatment.

What is claimed is:

1. A method for determining hemodynamic parameters during an extracorporeal hemotherapy, in which blood arrives via an arterial branch of an extracorporeal circuit in fluid communication with an arterial section of a fistula into a dialyzer or into a filter of a hemotherapeutic device, and is recirculated via a venous branch of the extracorporeal circuit which is in fluid communication with a venous section of the fistula, a blood pump being connected in the extracorporeal circuit, comprising the steps of:

measuring a physical or chemical characteristic quantity $X_A$ of the blood in the arterial branch, the physical or chemical characteristic quantity being a blood property which has a different value in the venous branch than in the blood flowing to the fistula;

varying a delivery rate of the blood pump in the extracorporeal circuit;

storing the values of an extracorporeal blood flow Q stipulated by the delivery rate and the measured values of the physical or chemical characteristic quantity of the blood in the arterial branch, a stored sequence of value pairs $X_A$ and $Q_B$ thereby resulting; and determining a value of the extracorporeal blood flow from the stored sequence of value pairs $X_A$ and $Q_B$, at which value, after it is exceeded, the amount of the change in the physical or chemical characteristic quantity $X_A$ within a specific extracorporeal blood flow interval is greater than a predetermined limiting value, fistula flow being inferred from the determined blood flow value.

2. The method as defined by claim 1, wherein a characteristic function curve existing in the sequence of the value pairs is represented by a predetermined first subfunction $X_A(Q_B)$ for value pairs smaller than the determined blood flow value; the characteristic function curve existing in the sequence of the value pairs is represented by a predetermined second subfunction $X_A(Q_B)$ for value pairs greater than the determined blood flow value; and the intersection point of the first and second subfunction is determined to exactly determine the fistula flow $Q_F$.

3. The method as defined by claim 2, wherein the first subfunction $X_A(Q_B)$ is extrapolated approaching a blood flow value of 0 to determine the average value $X_B$ of the physical or chemical characteristic quantity in the venous blood of the patient.

4. The method as defined by claim 3, wherein the first subfunction has the form:

$X_A(Q_B) = (\gamma + \epsilon Q_B)/(\epsilon + Q_B)$ where $\gamma = (CO - Q_F) X_B$, $\delta = X_V$, $\epsilon = CO - Q_F$ \quad (1)

$X_V$ being the physical or chemical characteristic quantity in the venous branch and CO being a cardiac output.

5. The method as defined by claim 3, wherein the second subfunction has the form:

$X_A(Q_B) = \alpha/Q_B + \beta$ where $\alpha = Q_F X_B (1 - Q_F/CO) + Q_F^2 X_V/CO - Q_F X_V$, $\beta = X_V$ \quad (2)

$X_V$ being the physical or chemical characteristic quantity in the venous branch and CO being a cardiac output.

6. The method as defined by claim 3, wherein the physical or chemical characteristic quantity $X_A$ measured in the arterial branch is the temperature $T_A$ of the blood.

7. The method as defined by claim 2, wherein the first subfunction has the form:

$$X_A(Q_B) = (\gamma + \delta \cdot Q_B)/(\epsilon + Q_B)$$

where $\gamma = (CO - Q_F)X_B$, $\delta = X_V$, $\epsilon = CO - Q_F$ (1)

$X_V$ being the physical or chemical characteristic quantity in the venous branch and CO being a cardiac output.

8. The method as defined by claim 7, wherein the second subfunction has the form:

$$X_A(Q_B) = \alpha/Q_B + \beta$$

where $\alpha = Q_F X_B(1 - Q_F/CO) + Q_F^2 X_V/CO - Q_F X_V$, $\beta = X_V$ (2)

$X_V$ being the physical or chemical characteristic quantity in the venous branch and CO being the cardiac output.

9. The method as defined by claim 7, wherein the physical or chemical characteristic quantity $X_A$ measured in the arterial branch is the temperature $T_A$ of the blood.

10. The method as defined by claim 2, wherein the second subfunction has the form:

$$X_A(Q_B) = \alpha/Q_B + \beta$$

where $\alpha = Q_F X_B(1 - Q_F/CO) + Q_F^2 X_V/CO - Q_F X_V$, $\beta = X_V$ (2)

$X_V$ being the physical or chemical characteristic quantity in the venous branch and CO being a cardiac output.

11. The method as defined by claim 10, wherein the physical or chemical characteristic quantity $X_A$ measured in the arterial branch is the temperature $T_A$ of the blood.

12. The method as defined by claim 2, wherein the physical or chemical characteristic quantity $X_A$ measured in the arterial branch is the temperature $T_A$ of the blood.

13. The method as defined by claim 1, wherein the physical or chemical characteristic quantity $X_A$ measured in the arterial branch is the temperature $T_A$ of the blood.

14. A device for determining hemodynamic parameters during an extracorporeal hemotherapy, in which blood arrives via an arterial branch of an extracorporeal circuit in fluid communication with an arterial section of a fistula, into a dialyzer or into a filter, and is recirculated via a venous branch of the extracorporeal circuit, which is in fluid communication with a venous section of the fistula, a blood pump being connected in the extracorporeal circuit, comprising:

an arterial measuring device for measuring a physical or chemical characteristic quantity $X_A$ of the blood in the arterial branch, the physical or chemical characteristic quantity being a blood property which has a different value in the venous branch than in the blood flowing into the fistula;

a control unit for altering the delivery rate of the blood pump;

a memory unit for storing the values of an extracorporeal blood flow $Q_B$ predetermined by a delivery rate of the blood pump and the values of the physical or chemical characteristic quantity $X_A$ measured using arterial measuring device, a stored sequence of value pairs $Q_B$ and $X_A$ thereby resulting; and a processor able to determine a value of the extracorporeal blood flow from the stored sequence of value pairs $Q_B$ and $X_A$, at which value, after it is exceeded, the amount of the change in the physical or chemical characteristic quantity within a specific blood flow interval is greater than a predetermined limiting value, a fistula flow $Q_F$ being inferable from the determined blood flow value.

15. The device as defined by claim 14, wherein the processor infers an average value $X_B$ of the physical or chemical characteristic quantity in the venous blood and/or the cardiac output (l/min) CO from the determined fistula flow $Q_F$.

16. The device as defined by claim 15, wherein the physical or chemical characteristic quantity of the blood to be measured in the arterial branch is the blood temperature $T_A$, and the arterial measuring device is a temperature-measuring device.

17. The device as defined by claim 14, wherein the physical or chemical characteristic quantity of the blood to be measured in the arterial branch is the blood temperature $T_A$, and the arterial measuring device is a temperature-measuring device.

18. A dialyzer having a device according to claim 14.

* * * * *

UNITED STATES PATENT AND TRADEMARK OFFICE
CERTIFICATE OF CORRECTION

PATENT NO. : 5,866,015
DATED : February 2, 1999
INVENTOR(S) : KRÄMER, M.

It is certified that error appears in the above-identified patent and that said Letters Patent is hereby corrected as shown below:

Column 9, Line 37 change "... display unit 37. To determine..." to -- ... display unit 37.
 To determine... --.

Column 10, Line 49 change "...by claim 3, ..." to -- ...by claim 2, ... --.

Column 10, Line 51 change "... $=(\gamma + \in Q_\beta)/...$" to -- ... $=(\gamma + \delta\, Q_\beta)/...$ --.

Column 11, Line 3 change "... $(\gamma + \delta^\circ\, Q_\beta)/ ...$" to -- ... $(\gamma + \delta\, Q_\beta)/ ...$ --.

Signed and Sealed this

Fifteenth Day of February, 2000

Q. TODD DICKINSON

*Attest:*

*Attesting Officer*  *Commissioner of Patents and Trademarks*